(12) United States Patent
Powers et al.

(10) Patent No.: US 7,592,001 B2
(45) Date of Patent: Sep. 22, 2009

(54) HIGH ASPECT RATIO METAL PARTICLES AND METHODS FOR FORMING SAME

(75) Inventors: Kevin William Powers, Gainesville, FL (US); Marie Kissinger, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 786 days.

(21) Appl. No.: 10/909,587

(22) Filed: Aug. 2, 2004

(65) Prior Publication Data

US 2006/0024250 A1    Feb. 2, 2006

(51) Int. Cl.
*A61K 8/18*    (2006.01)
(52) U.S. Cl. ........................................................ 424/61
(58) Field of Classification Search .................. None
See application file for complete search history.

(56) References Cited

U.S. PATENT DOCUMENTS

| | | | | |
|---|---|---|---|---|
| 4,693,916 A | * | 9/1987 | Nagayama et al. | 427/397.7 |
| 4,755,456 A | * | 7/1988 | Sugimoto | 430/569 |
| 4,944,985 A | * | 7/1990 | Alexander et al. | 428/570 |
| 5,320,703 A | * | 6/1994 | Ikeda et al. | 117/68 |
| 5,654,133 A | * | 8/1997 | Oikawa | 430/569 |
| 5,814,370 A | * | 9/1998 | Martino et al. | 427/213.35 |
| 6,074,811 A | * | 6/2000 | Saitou | 430/567 |
| 6,586,098 B1 | * | 7/2003 | Coulter et al. | 428/403 |
| 2003/0100778 A1 | * | 5/2003 | Cunningham et al. | 549/533 |

OTHER PUBLICATIONS

Lakshmi et al "Sol-gel Template synthesis of semiconductor oxide micro- and nanostructures" Chem. Mater., 1997, 9, 2544-2550.*
Cheng et al "Fabrication and characterization of nanotublar semiconductor oxides In2O3 and Ga2O3" J. Mater. Chem., 2001, 11, 2901-2902.*
Y. Zhou et al. "A Novel Ultraviolet Irradiation Technique for Shape-Controlled Synthesis of Gold Nanoparticles at Room Temperature" Chem. Mater., 1999, 11:2310-2312.

* cited by examiner

*Primary Examiner*—M P Woodward
*Assistant Examiner*—Bethany Barham
(74) *Attorney, Agent, or Firm*—Saliwanchik, Lloyd & Saliwanchik

(57) ABSTRACT

An electroless method of forming high aspect ratio metal particles includes the steps of mixing a metal or metal salt with at least one acid to form an acidified metal halide salt solution, and mixing the solution with a supersaturated sol to form a sol comprising solution. Metal cations provided by the acidified metal salt are reduced to form a plurality of high aspect ratio metal particles. Instead of using a sol, an organic compound can be oxidized to generate the reducing agent. A metal comprising particle assembly includes a plurality of high aspect ratio metal platelets having an aspect ratio of a major dimension averaging from 10 to 200 times a nanoscale minor dimension of the platelet. The platelets can be used for nail polish, eye liner or the cores for medical delivery vehicles.

21 Claims, 6 Drawing Sheets

HIGH ASPECT RATIO METAL PARTICLES AND METHODS FOR FORMING SAME

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The invention related to high aspect ratio metal particles and methods for forming the same.

BACKGROUND

There are a wide variety of applications for metallic nanostructured particles. For example, high aspect ratio electrically conductive particles can be used in powders or smoke for military ordnance to produce obscuring fogs to scatter radar frequencies. These particles can also be used by themselves, or in paints and coatings for corrosion resistance, reflectivity, modification of electrical properties, or aesthetic purposes.

There are also numerous biotechnology-based applications for metallic nanostructured particles. Gold has been proven to be hypoallergenic and safe to use in a wide variety of biological applications. Spherical gold and silver nanoparticles are currently used as biological stains and/or conjugating agents. Micron size gold colloids are also currently being considered for drug delivery and/or gene delivery.

Current methods for forming metallic nanostructured particles include crystallization and/or mechanical methods, such as grinding. Grinding can be used to convert a roll metal sheet having a nanoscale thickness into platelets. However, grinding is known to produce a significant range of platelet thickness and sizes. Nanoscale layers can also be formed by electroless deposition or by electroplating. However, electroplating systems use toxic chemicals and environmental/disposal costs are high. In addition, plating generally forms films, rather than discrete particles. Non-aqueous techniques incorporating gold salts and a variety of reducing agents have also been disclosed for forming certain metallic nanostructured particles.

In some applications, a substantially monodisperse size distribution of platelets is desirable. High aspect particulate systems are difficult to classify by either size or shape. It is not currently practical to sieve or otherwise separate broad distributions of flake sizes or shapes into narrowing distribution groups particularly for powders with large fractions below mesh 400 (38 microns sieve opening).

SUMMARY OF THE INVENTION

An electroless method of forming high aspect ratio metal particles includes the steps of mixing a metal or metal salt with at least one acid to form an acidified metal halide salt solution, and mixing the solution with a supersaturated sol to form a sol comprising solution. Metal cations provided by the acidified metal salt are reduced and crystallized to form a plurality of high aspect ratio metal particles. The metal is generally a noble metal, such as gold. In one embodiment, the method further includes the steps of gelling the sol to form a gel, heating the gel, where the plurality of high aspect ratio metal particles nucleate and grow and become embedded in a dried gel. The dried gel is then removed. The removing step can comprise exposing the dried gel to an acid or a base.

The sol can be a silica sol, such as TMOS or TEOS. The sol comprising solution can include at least one solvent. The solvent can be an alcohol, ketone or an acetate.

At least one dimension, such as the thickness, of the plurality of metal particles can be nanoscale. An average aspect ratio of the plurality of nanoscale metal particles can be at least 100. The size distribution of the plurality of metal particles is substantially monodisperse. As used herein, the phrase "substantially monodisperse size distribution" refers to at least 90% of the particles being within 1 standard deviation of the mean particle size in the distribution.

An electroless method of forming metal particles includes the steps of dissolving at least one organic compound in a solvent to form a solution, mixing a metal halide salt with the solution, and oxidizing the organic compound, where oxidation of the organic compound generates at least one reducing agent. The reducing agent reduces metal ions from the metal halide salt to form a plurality of metal particles. The organic compound can comprises a sugar, such as sucrose.

A metal comprising particle assembly includes a plurality of high aspect ratio metal platelets having an aspect ratio of a major dimension averaging from 10 to 200 times a minor dimension (thickness) of the platelets. The minor dimension can be between 20 nm and 1 micron. In a preferred embodiment, the plurality of platelets provide a substantially monodisperse size distribution and the metal comprises gold. The platelets can be used for reflective or conductive pigments, nail polish, eye liner or the cores for medical delivery vehicles.

BRIEF DESCRIPTION OF THE DRAWINGS

A fuller understanding of the present invention and the features and benefits thereof will be obtained upon review of the following detailed description together with the accompanying drawings, in which.

DETAILED DESCRIPTION

Figure 1:
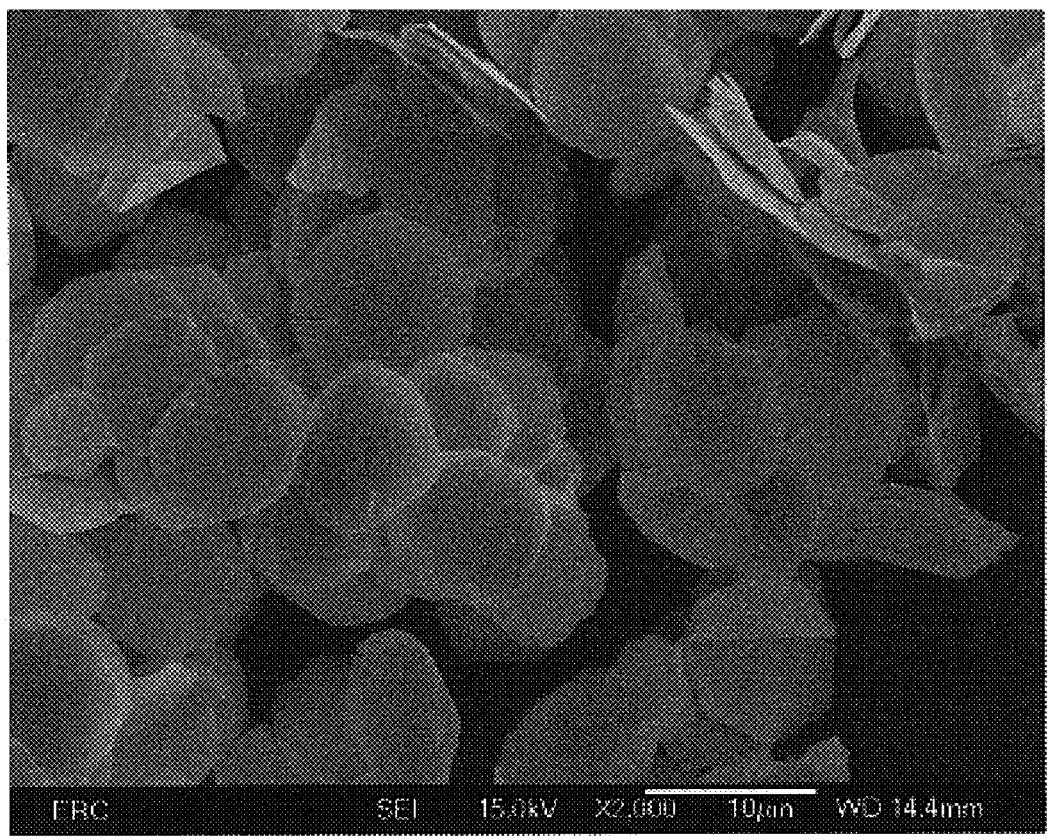
FIG. 1 is a scanned SEM image showing a plurality of Au platelets having diameters of about 7 to 10 μm formed using the sol-gel method according to an embodiment of the invention.

The present invention is more particularly described below and is intended to be illustrative only since numerous modifications and variations therein will be apparent to those skilled in the art. As used in the specification and in the claims, the singular form "a," "an," and "the" may include plural referents unless the context clearly dictates otherwise. Also, as used in the specification and in the claims, the term "comprising" may include the embodiments "consisting of" and "consisting essentially of."

The invention provides environmentally benign wet solution methods of producing high aspect ratio or super high aspect ratio (a≧100) and large surface area metal particles, such as platelets, rods or free floating films. As a wet solution technique, the invention is easily amenable to scale up. In certain applications, the high aspect ratio of the particles can save a large amount of expensive raw material, such as gold. As used herein the phrase "high aspect ratio" refers to an aspect ratio (a) of at least 10, and preferably at least 100. A super high aspect ratio refers to aspect ratios of greater than 100, such as 500 or 1,000.

Attainable particle sizes generally range from about 20 nanometers to several millimeters in the major dimension(s), and from about 10 nm to several microns and higher in the minor dimension. Aspect ratios of up to five hundred or more have been measured for some particles formed using the invention. In certain embodiments described herein, the particle size distribution produced by the invention is substantially monodisperse. As used herein, the phrase "substantially monodisperse size distribution" refers to at least 90% of the particles being within 1 standard deviation of the mean particle size in the distribution.

The metal is preferably one of the noble metals comprising Cu, Ag, Au, Pt, or Pd, or can be a noble metal comprising alloy. The size and shape of the metal particles obtained generally depends on parameters including the nucleation event, concentration of the metal in solution, pH, temperature, and reducing agent chemistry.

A sol-gel based electroless method of forming high aspect ratio metal particles includes the steps of mixing an acidified metal halide salt and a supersaturated sol, where metal cations provided by the acidified metal salt are reduced to form high aspect ratio metal particles. The sol can be a silica based sol, such as TMOS or TEOS. Other sols which can be used with the invention include those made from colloidal silica such as LUDOX® produced by Grace Davison, Columbia, Md. The particles in LUDOX® colloidal silica are discrete uniform spheres of silica which have virtually no internal surface area or detectable crystallinity. Sodium silicate sols can also be used. Silica sols are generally aqueous suspensions of very tiny (several nm scale) silica particles stabilized under basic conditions. These sols gel upon the addition of an acid, fluoride ion or other catalyst.

Other "gel" systems or viscosity enhancers such as gelatin or hydroxy cellulose are also expected to perform the same function as silica sols under proper conditions. Organic gels typically set up due to crosslinking of polymeric species, physical entanglement or intermolecular forces. The resulting systems are similar to inorganic gels (such as silica based gels) in terms of some Theological properties, restricted diffusion through the porous network and both continuous solid and continuous liquid phases. Gel systems incorporating both inorganic and organic constituents may also be used.

The sol-gel process is a versatile well-known low temperature solution process for making inorganic ceramic and glass materials. In general, the sol-gel process involves the transition of a system from a liquid "sol" (mostly colloidal) into a solid "gel" phase. Applying the sol-gel process, it is possible to fabricate ceramic or glass materials in a wide variety of forms including ultra-fine or spherical shaped powders, thin film coatings, ceramic fibers, micro porous inorganic membranes, monolithic ceramics and glasses, or extremely porous aerogel materials.

The starting materials used in the preparation of the "sol" are usually alkoxides. In a typical sol-gel process, the precursor is subjected to a series of hydrolysis and polymerization reactions to form a colloidal suspension, or a "sol". Hydrolysis of an alkoxide liberates alcohol and results in polymerized chains of metal hydroxide. For example, silica gels can be formed by hydrolysis of tetraethoxysilicate (TEOS; an alkoxide having the formula $Si(OC_2H_5)_4$) based on the formation of silicon oxide $SiO_2$ and ethyl alcohol $C_2H_5OH$ as noted below:

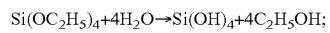

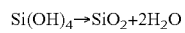

In one embodiment, a metal or metal salt is mixed with at least one acid, such as a mixture of nitric and hydrochloric acids (e.g. aqua regia) with metallic gold, or gold chloride, to form an acidified solution comprising the metal halide salt. The solution is then combined with a supersaturated silica sol in the presence of a solvent. The solvent is considered to be an integral part of the silica sol gel process. The solvent generally includes either water, an alcohol or a combination of the two. The sol is allowed to gel and then is heat treated to a temperature sufficient to preferably evaporate off all the solvent, including the water supplied by the acidified metal salt solution. For example, 200° C. has been found to be generally sufficient for this purpose. This process produces nanoscale metal platelets roughly spherical to hexagonal in shape embedded in the dried silica gel. The silica gel can then be dissolved using an acid or a base, such as hydrofluoric acid and KOH, respectively, thus leaving the dispersed gold platelets. The size of the gold platelets can be controlled by parameters including the concentration of metal salt and/or by adjusting conditions bearing on the morphology, such as pore size, surface area and density of the gel. These parameters include but are not limited to pH, solvent composition, silica content, precursor, catalyst selection, other additives, pre and post heat treatments, drying conditions (including supercritical drying) and drying rate.

A second sol-gel method embodiment uses a supersaturated silica sol in an acidic methanol water cosolvent system including a dissolved metal salt which promotes the formation of single crystal metal platelets in solution. As long as the water is acidified, a cosolvent is not required for the TMOS formulation because the rapid TMOS hydrolysis process provides significant methanol and by the time the TMOS is fully hydrolyzed the resulting silicic acid ($H_2O_3Si$) is water soluble. If the sol is TEOS, a cosolvent is generally required, such as an alcohol, a ketone (e.g. acetone) or an acetate (e.g. ethylacetate) because the hydrolysis of TEOS is slow and TEOS is insoluble in water and thus phase separates from water.

The solution formed platelets formed from gold comprising salts using this embodiment have been found to be nearly perfectly formed, growing as flat triangular and/or hexagonal crystals of gold. Platelets grown in this fashion range in size from less than 20 nanometers to over 2 millimeters. Larger platelets can be prepared by this method and there is the potential to grow free thin films of any size. Gold crystals have been found to grow along the (111) crystal plane.

Although not needed to practice the claimed invention, Applicants, not seeking to be bound to theory, present the following mechanism for metal particle formation in a gel-like environment provided by the sol in an acidic environment. Specifically, the growth of the metal platelets is believed to be coordinated by the C—O—H bond from the surfactants or methanol/silanol. Any of a number of alcohols and other organic compounds especially when oxidized may promote this type growth. A variety of other functional groups formed from the organic additives may participate in reduction of the metal salt and in the shape selectivity of the ensuing particles. The silica itself is not believed to be generally necessary for the promotion of platelet growth, but in certain embodiments aids in their formation and the control of the size and shape.

The effect of the silica gel in the monodisperse system is believed to control the rate of diffusion of metal ions, reducing agents and surface active agents to the nucleation site. A diffusion limited reaction and a depletion zone are believed to be formed around each nucleation site. This, results in a narrow size distribution, and permits the formation of asymmetric high aspect ratio particles. In the fully gelled system, this mechanism has the effect of producing a substantially uniform particle size distribution and also interferes with crystallization enough to produce rounded rather than geometric platelets.

Another method embodiment of the invention is referred to as a solution method. The solution method combines a metal containing salt with a soluble organic compound in solution. The organic compound is slowly oxidized by heat or through the use of an oxidizing agent. Oxidation of the organic compound produces a slow but steady supply of surfactant/reducing agents, such as carboxylic acids, aldehydes, ketones and/or amines, which act as coordinating agents by promoting the controlled growth of triangular or hexagonal metal crystals. This process is controlled by a variety of parameters such as temperature, pH, concentrations of reactants, solvent system and method of nucleations (homogeneous, heterogeneous or seeding). Thus, the nucleation and growth rate and morphology of the particles can be controlled. Rod shaped particles can also be produced under specific growth conditions.

Metal particles according to the invention are expected to have a broad range of applications. Due to the relatively high cost of precious metals such as Au, Pt and Pd, the resulting savings provided when high aspect ratio particles provided by the invention are used is expected to be particularly attractive for such applications including these metals. For example, decreasing the thickness of a platelet by 50% saves a proportionate amount of the expensive metal. Particles according to the invention can be consistently produced with thicknesses on the order of 10's of nanometers, such as 10, 20, 30, 40, 50, 60, 70, 80, 90 or 100 nm thick particles having a thickness within a standard deviation of less than 10%, as well the standard deviation of the particle cross sectional areas being within 10%. Although applications below are described below relative to Au particles, the invention is in no way limited to Au particles or pure elements.

Gold platelets can be used in powders or smoke used in military ordnance to produce obscuring fogs that scatter infrared, microwave and radar frequencies. If incorporated in random orientations in coatings, such coatings will scatter radar and or infrared energies giving thus providing utility as radar dispersive coatings and protection against the effects of electromagnetic pulse (emp). If embedded in silica glass or other microwave transparent dielectric, the resulting particle composite can be used to uniformly disperse microwave energy in commercial microwave ovens.

Jewelry and coating applications for the invention exist because of the high aspect ratio and smooth reflective surface of platelets which can be produced using the invention. Current electroplating systems use toxic chemicals and the environmental/disposal costs are high. Gold leaf and related decorative paints and coatings rely on physical methods of making irregular gold platelets, such as grinding, which cannot provide the controlled size and high aspect ratios provided by the invention. Platelets according to the invention can also be used by themselves or in paints and coatings to gold plate surfaces or produce pearlescent gold paints and coatings for corrosion resistance, reflectivity or aesthetic purposes. For example, a plurality of platelets mixed with a solvent base can be used for nail polish or eye liner.

A dried or dispersed pigment comprising high aspect particles according to the invention can be injected under the skin or other endothelial membrane for modifying the properties and/or appearance of the membrane for uses including tattoos or body jewelry. In another related application, embedding a sufficient concentration of high aspect ratio particles or gold rods through the dermal layer can provide an electrically conductive pathway that can be used for transmitting electrical power and/or electrical signals through the skin without opening the skin and risking infection. This arrangement may allow electrical signals to reach embedded appliances within patients such as pacemakers, without opening a surgical window. Platelets can be surface modified by a wide variety of techniques such as thiol based coupling agents to provide optimum dispersion. Orientation of platelets can be controlled by a binder solvent system and the coating efficiency controlled by optimum combination of different platelet sizes.

There are several biological applications for particles provided by the invention. As noted above, gold has been proven hypoallergenic and safe for biological applications. Nanosize platelets can be used in place of spherical gold nanoparticles as biological stains and/or conjugating agents. The platelets have an advantage over current gold colloids in that they provide a high aspect ratio which may improve their diffusive properties and increases light reflection, thus making them better stains. Platelets according to the invention thus have the potential to replace the nanocolloidal gold particles now used for histological stains.

Micron or larger size gold colloids are also currently used for drug delivery platforms where a gene, plasmid or protein layer coats the metal particle. In these applications, the high molecular weight of gold allows entry of the coated gold particle through the skin when propelled, such as by an air gun. High aspect ratio gold particles according to the invention are expected to provide higher efficacy as compared to currently available colloids through their high surface area to volume ratio. Conventional drug delivery platforms on metal particles use nanosized spherical colloidal gold particles or core shell particles. Platelets of similar size have an advantage by presenting larger surface areas with potentially better mobility through tissues to the conjugation site.

The regular shape of particles which can be produced using the invention also make them amenable to micromanipulation for the construction of conductive nanostructures for microelectromechanical systems (MEMS). High aspect ratio particles or free thin films of gold can be used for plating, metallization or other applications requiring an electroless metallic coating on any substrate. The platelets can be applied by spray, painting or sedimentation and solvent or binders removed by heat or evaporation leaving the pure gold film. The high aspect ratio of the platelets also gives good surface area in contact with a substrate for better adherence. Availability of platelets according to the invention may lead to new or improved methods of metallization for microelectronic components. Such particles may also be useful for plating bulk or micro optical components. Unlike vapor or electrolytic gold, the platelet surface can be chemically tailored to make them more adherent to specific substrates preventing delamination. Coating thicknesses can also potentially be better controlled by adjusting the metal to binder/solvent ratio or by using multiple coating application.

For general scientific applications, platelets can be used as model high aspect ratio powders for the study of light scattering, sedimentation, rheology and other techniques dependent on shape specific properties.

When grown to millimeter size or greater, platelets can be seen by the naked eye and can be incorporated into paints, coatings, glazes, glass or plastic bodies for decorative purposes including cosmetics. Cosmetics such as nail polish or eye shadow can be produced with unique appearance and properties. In this embodiment, particles according to the invention are mixed in a solvent base such particles can also be used for body paint or permanent metallic tattoos.

In some countries it is popular to consume gold flakes as a nutritional supplement and/or as a decorative garnish. The high surface area to weight ratio of particles according to the invention may enhance their effectiveness for these applications over traditionally produced gold powders. The high surface area to volume ratio of particles according to the invention also makes these particles ideally suited for use as catalysts.

EXAMPLES

The present invention is further illustrated by the following specific example, which should not be construed as limiting the scope or content of the invention in any way.

Example 1

Sol gel derived Au Flakes

One (1) ml of 0.65 molar Au in aqua regia was mixed with 2 ml of concentrated nitric acid in 30 ml deionized water. Sixty (60) ml of tetramethoxysilane (TMOS) was added slowly to avoid boiling over and the mixture was allowed to gel. Gellation was fairly rapid. The resulting gel was dried over a period of 24 hours in a pinhole drying container to control drying rate with a ramped drying schedule that increases the temperature uniformly from ambient to 200° C. The dried gel was held at 200° C. for six hours before cooling. The resulting porous dried gel was then dissolved in 25% HF solution releasing circular gold platelets that were formed in the gel matrix. The gold platelets were centrifuged from the HF solution, rinsed and stored in methanol or other selected organic solvent. The size and morphology of the gold platelets formed was found to be controllable by modification of the silica gel formulation, density, pore structure and drying schedule, and through the selection of appropriate reaction conditions and concentrations of the gold salt.

Figure 2:
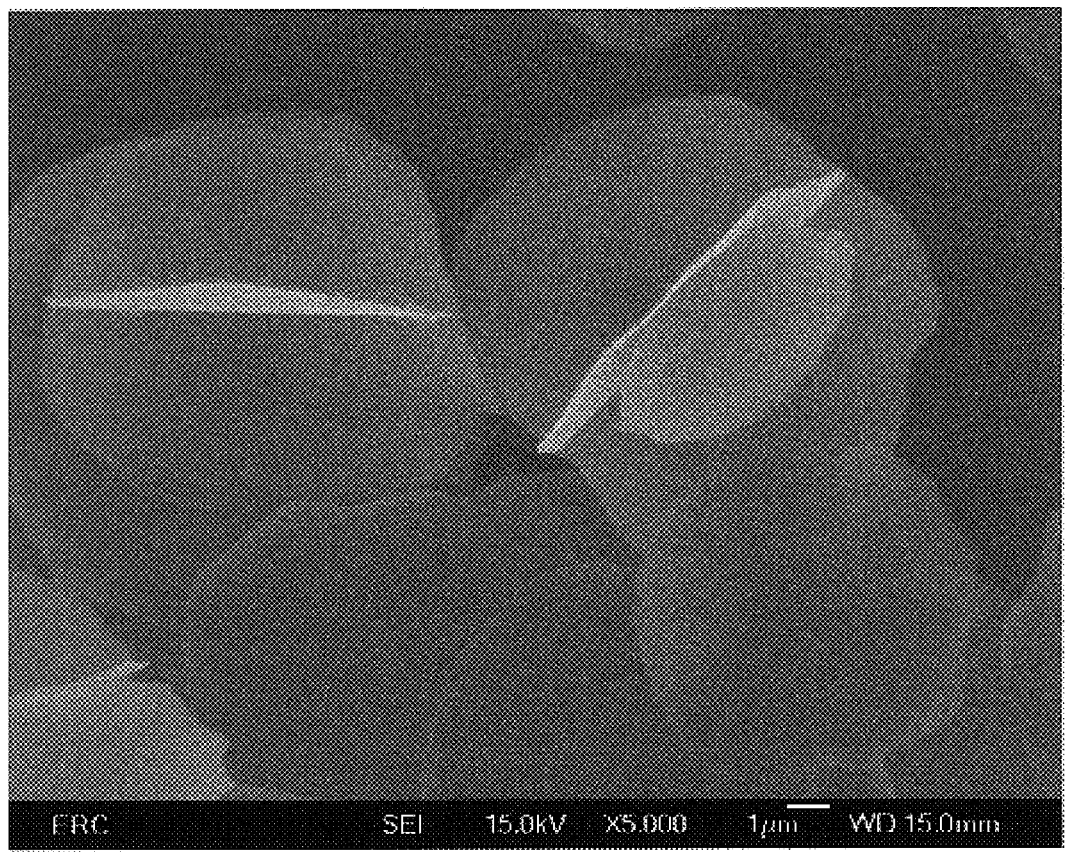
FIG. 2 is a scanned SEM image showing the nanoscale thickness of some platelets shown in FIG. 1.
Figure 3:
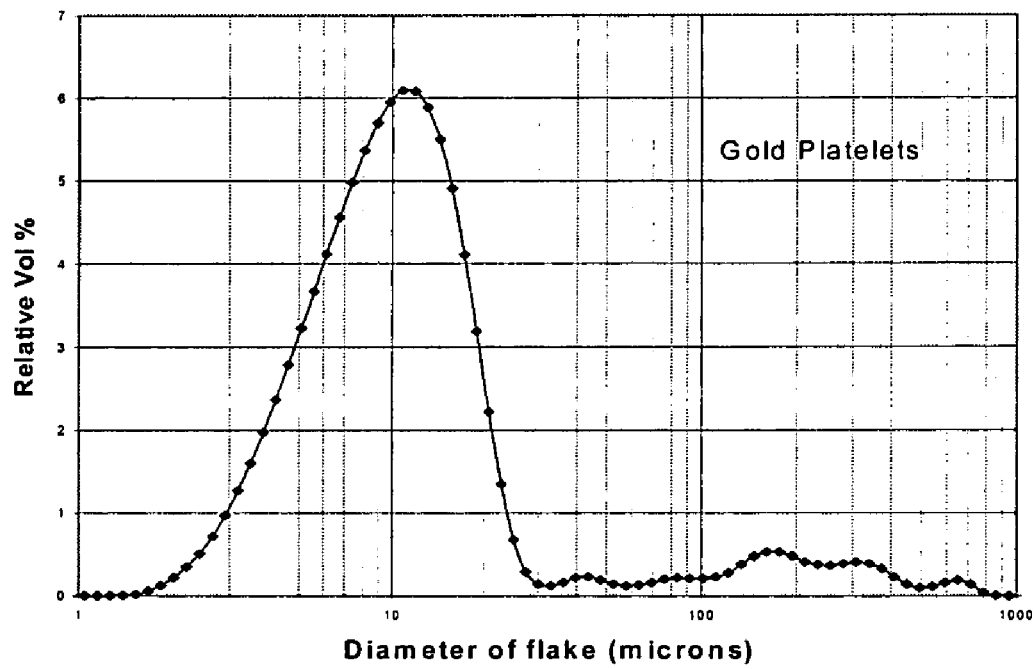
FIG. 3 is a laser diffraction derived distribution of diameters of Au platelets formed using the sol-gel method.
Figure 4:
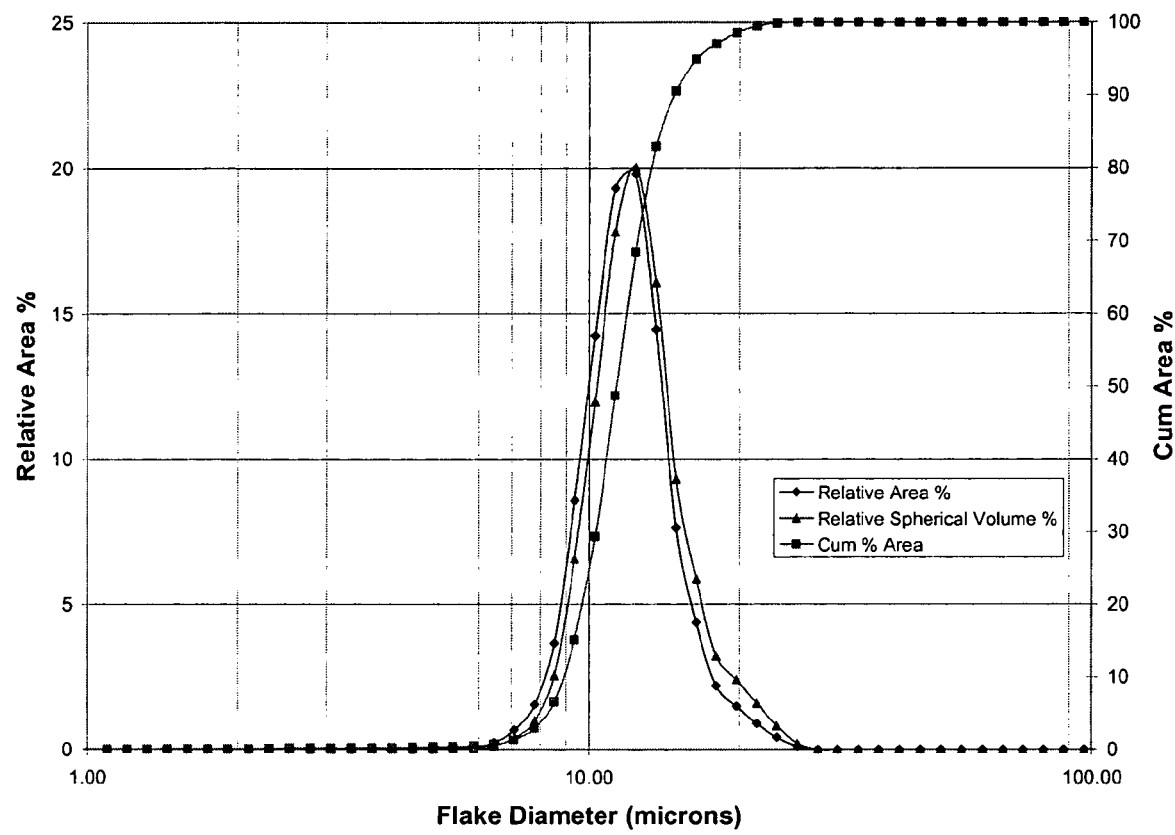
FIG. 4 is an image analysis derived circular area equivalent diameter of sol-gel derived Au platelets.

FIG. 1 is a SEM showing a plurality of Au platelets formed as described above using the sol-gel method having diameters of about 7 to 10 μm. FIG. 2 is a SEM showing the nanoscale thickness of some platelets shown in FIG. 1. FIG. 3 is a laser diffraction derived distribution of diameters of the Au platelets. The fraction at diameters of about 30 μm, or more, is due to agglomeration. FIG. 4 is an image analysis derived circular area equivalent diameter of sol-gel derived Au platelets. The circular area equivalent diameter means each particle is measured and reported as the diameter of a circle that has the equivalent area.

Example 2

Au crystals via the Solution Method

A gold chloride comprising salt solution formed from 1 ml of 0.65 molar Au in aqua regia with 2 ml of concentrated nitric acid in 30 ml deionized water was mixed with 20 ml of a 1.5 molar sucrose solution. As noted above, oxidation of organic compounds such as sucrose produces a slow but steady supply of surfactant/reducing agents, which act as coordinating agents by promoting the controlled growth of generally triangular or hexagonal metal crystals.

Figure 5:
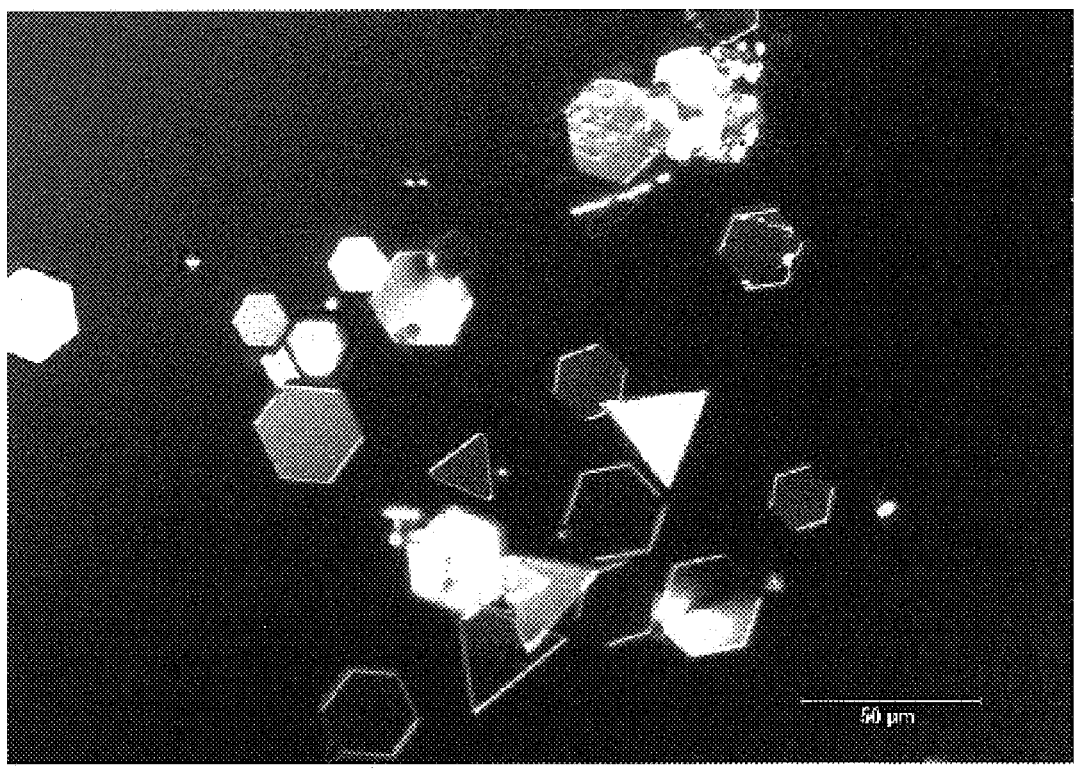
FIG. 5 is a scanned optical micrograph of Au crystals grown by the solution method, according to another embodiment according to the invention.
Figure 6:
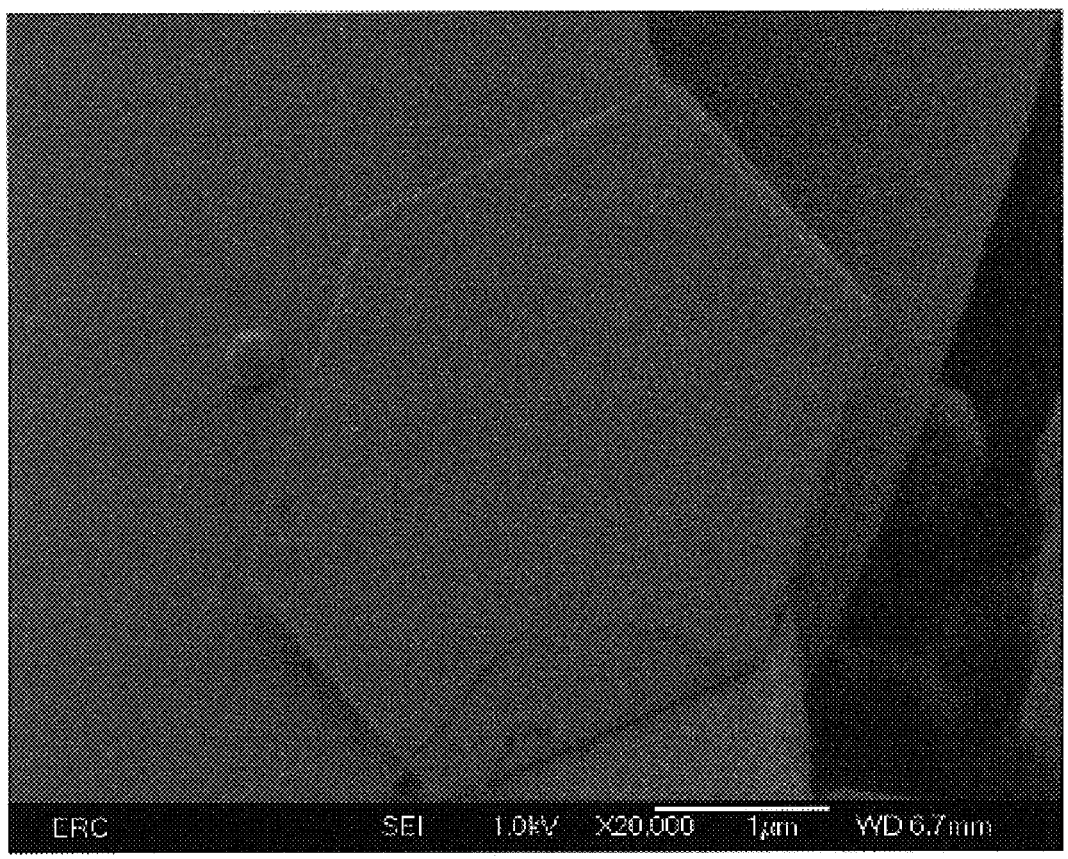
FIG. 6 is a scanned SEM image showing the dimensions of a Au crystal grown using the solution method.

The solution was heated at 60° C. for 72 hours to allow for the nucleation and growth of the gold crystals. The solution was then centrifuged to remove the gold particles and then rinsed in deionized water and resuspended in 20 ml deionized water with 1 ml of 30% hydrogen peroxide. This solution was heated at 60° C. for 24 hours to remove any remaining organic constituents. The gold particles were then centrifuged, rinsed and stored in methanol or other selected organic solvent. FIG. 5 is an optical micrograph of Au crystals grown by the solution method described above. FIG. 6 is a SEM showing the dimensions of a Au crystal grown using the solution method.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. An electroless method of forming high aspect ratio metal particles, comprising the steps of:
   mixing a metal or metal salt with at least one acid to form an acidified metal halide salt solution, and
   mixing said acidified metal halide salt solution with a supersaturated sol to form a sol comprising solution, wherein metal cations provided by said acidified metal halide salt are reduced and crystallized to form a plurality of high aspect ratio metal particles that are individually dispersed single crystal metal platelets.

2. The method of claim 1, further comprising the steps of:
   gelling said sol to form a gel;
   heating said gel, wherein said plurality of high aspect ratio metal particles nucleate and grow, and become embedded in a dried gel, and
   removing said dried gel.

3. The method of claim 2, wherein said removing step comprises exposing said dried gel to an acid or a base.

4. The method of claim 1, wherein said sol is a silica sol, and wherein the plurality of metal particles have an average aspect ratio of at least 100 and a high surface area to volume ratio.

5. The method of claim 1, wherein said sol consists of tetramethoxysilane or tetraethoxysilicate.

6. The method of claim 1, wherein said sol comprising solution includes at least one solvent.

7. The method of claim 6, wherein said solvent is at least one selected from the group consisting of alcohols, ketones and acetates.

8. The method of claim 1, wherein at least one dimension of said plurality of metal particles are nanoscale.

9. The method of claim 8, wherein an average aspect ratio of said plurality of metal particles is at least 500.

10. The method of claim 1, wherein a size distribution of said plurality of metal particles is substantially monodisperse.

11. The method of claim 1, wherein said metal comprises gold.

12. An electroless method of forming high aspect ratio metal particles, comprising the steps of:
   mixing a metal or metal salt with at least one acid to form an acidified metal halide salt solution, and
   mixing said acidified metal halide salt solution with a supersaturated sol to form a sol comprising solution, wherein metal cations provided by said acidified metal halide salt are reduced and crystallized to form a plurality of high aspect ratio metal particles that are individually dispersed metal platelets, and wherein the supersaturated sol is metal-free.

13. The method of claim 12, further comprising the steps of:
gelling said sol to form a gel;
heating said gel, wherein said plurality of high aspect ratio metal particles nucleate and grow, and become embedded in a dried gel, and
removing said dried gel.

14. The method of claim 12, wherein said removing step comprises exposing said dried gel to an acid or a base.

15. The method of claim 12, wherein the plurality of metal particles have an average aspect ratio of at least 100 and a high surface area to volume ratio.

16. The method of claim 12, wherein the sol consists of tetramethoxysilane or tetraethoxysilicate.

17. The method of claim 12, wherein said sol comprising solution includes at least one solvent.

18. The method of claim 17, wherein said solvent is at least one selected from the group consisting of alcohols, ketones and acetates.

19. The method of claim 12, wherein at least one dimension of said plurality of metal particles are nanoscale.

20. The method of claim 12, wherein the sol is a silica sol.

21. The method of claim 12, wherein a size distribution of said plurality of metal particles is substantially monodisperse.

* * * * *

UNITED STATES PATENT AND TRADEMARK OFFICE
CERTIFICATE OF CORRECTION

| | |
|---|---|
| PATENT NO. | : 7,592,001 B2 |
| APPLICATION NO. | : 10/909587 |
| DATED | : September 22, 2009 |
| INVENTOR(S) | : Kevin William Powers et al. |

It is certified that error appears in the above-identified patent and that said Letters Patent is hereby corrected as shown below:

Column 3,
Line 50, "Theological properties" should read --rheological properties--.

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,592,001 B2  Page 1 of 1
APPLICATION NO. : 10/909587
DATED : September 22, 2009
INVENTOR(S) : Powers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1254 days.

Signed and Sealed this

Twenty-first Day of September, 2010

David J. Kappos
*Director of the United States Patent and Trademark Office*